US00PP08883P

United States Patent [19]

van Andel

[11] Patent Number: Plant 8,883

[45] Date of Patent: Sep. 6, 1994

[54] MINI-SPRAY CARNATION PLANT NAMED 'STAGIBORD'

[75] Inventor: Jacob van Andel, Aalsmeer, Netherlands

[73] Assignee: Van Staaveren, B. V., Aalsmeer, Netherlands

[21] Appl. No.: 100,073

[22] Filed: Jul. 29, 1993

Related U.S. Application Data

[63] Continuation of Ser. No. 770,401, Oct. 3, 1991, abandoned.

[51] Int. Cl.[5] ..... A01H 5/00

[52] U.S. Cl. ..... Plt./70.2

[58] Field of Search ..... Plt. 70.1, 70.2, 70.6

*Primary Examiner*—Howard J. Locker

*Attorney, Agent, or Firm*—Tilton, Fallon, Lungmus & Chestnut

[57] ABSTRACT

A new and original variety of mini-spray carnation particularly distinguished by its small tyrian purple flat blossoms, which are bloomed profusely and intermittently from Spring through Fall in clusters borne on erect stems branching from the main stem of an upright bush that has a height of about 100–120 cm.

1 Drawing Sheet

This application is a continuation application Ser. No. 07/770,401 filed Oct. 3, 1991 abandoned.

BACKGROUND OF THE NEW PLANT

This new carnation plant originated as a sport of the variety Statropur (U.S. Plant Pat. No. 7,849) being grown at our nursery in Aalsmeer, Holland. This particular sport was discovered by me and attracted my attention because of its unusual flat tyrian purple colored flowers and the overall high quality of the plant growth. This new carnation plant is a sport of unknown causation. The sport was found as a branch of Statropur. Stagibord differs from the parental cultivar in its overall plant height, the color of its petals, the color of its stigma and style and in its fruit fertility. Listed below in Table 1 is a comparison of Stagibord with Statropur and other known sports of Statropur. The other sports provided in Table 1 are subjects of copending applications. Serial numbers for these applications are provided for in the Table.

TABLE 1

| | STA-GIBORD | STATROPUR | STAGILAC |
|---|---|---|---|
| SERIAL NO.: | 08/100,073 | 07/611,504 | 08/099,271 |
| RELATED APPLI-CATIONS: | 08/100,073 is a Continuation of 07/770,401 (Abandoned) | — | 08/099,271 is a Continuation of 07/756,798 (Abandoned) |
| PATENT NO.: | — | U.S. Plant Pat. No. 7,849 | — |
| PETAL BODY: | RHS 57-B + RHS 57-A ("Mottled Portion") | RHS 74-B | RHS 74-B |
| PETAL BASE: | RHS 155-D | White | RHS 155-D |
| REVERSE SIDE: | RHS 62-A | White | RHS 72-C |
| STIGMA: | RHS 64-B | White | RHS 155-D |
| STYLE: | RHS 64-B | White | RHS 155-D |
| HEIGHT: | 100–200 cm. (average) | 150 cm. (average) | 100–110 cm. (average) |
| DIS-COLORATION AFTER FULL BLOOM: | Slight | None | Slight |
| FERTILE FRUIT: | No | Yes | No |

TABLE 1-continued

| | STAVIOLET | STAGIROS |
|---|---|---|
| SERIAL NO.: | 08/098,842 | 08/099,780 |
| RELATED APPLICATIONS: | 08/098,842 is a Continuation of 07/770,403 (Abandoned) | 08/099,780 is a Continuation of 07/770,402 (Abandoned) |
| PATENT NO.: | — | — |
| PETAL BODY: | RHS 74-A | RHS 73-A + RHS 73-D ("Mottled Portion") |
| PETAL BASE: | RHS 155-D | RHS 155-D |
| REVERSE SIDE: | RHS 155-D | RHS 73-D |
| STIGMA: | RHS 155-D | RHS 155-D |
| STYLE: | RHS 155-D | RHS 155-D |
| HEIGHT: | 100–110 cm. (average) | 100 cm. (average) |
| DISCOLORATION AFTER FULL BLOOM: | Slight | Slight |
| FERTILE FRUIT: | No | No |

Asexual propagation of this plant was done by means of cuttings under my direction at Aalsmeer; and propagation of this new plant was continued through successive generations to determine whether the novel characteristics of this plant would be retained from generation to generation and whether its homogeneity could be assured. This proved to be successful and this new carnation variety is now being propagated at Aalsmeer.

DESCRIPTION OF THE DRAWING

My new carnation cultivar is illustrated by the accompanying full-color photographic drawing, which shows blooming portions of spray stems with umbel clusters of buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to the R.H.S.

Colour Chart published by The Royal Horticultural Society of London, England.

THE PLANT

Origin: Sport.
Parentage: Statropur U.S. Plant Pat. No. 7,849).
Classification:
*Botanic.*—Dianthus hybrid.
*Commercial.*—Mini-spray carnation.
Form: Strong, upright bush.
Height: 100–120 cm. in average.
Growth rate: Fast.
Main stem:
*Length.*—In average, about 110 cm.
*Growth.*—Strong and upright.
*Branching character.*—The main stem has 7–8 side branches and each side branch has 2 branches and each of these branches has 1–2 branches.
Foliage:
*Number of leaves.*—22–26.
Leaf:
*Size.*—Length: 7–11 cm. Width: -2 cm.
*Shape.*—Elliptical.
*Margins.*—Entire, straight.
*Texture.*—Smooth.
*Color.*—Upper side — 137-A. Under side — 137-C.

THE BUD

Size: Medium.
*Diameter.*—Averaging about 3 mm.
*Length.*—Averaging about 20 mm.
Shape: Cylindrical, long and pointed.
Rate of opening: Fast.
Calyx:
*Shape.*—Cylindrical. The calyx is formed out of 5 pointed sepals of about 5 mm. which are joined at the lower point and are sharply pointed at the apex.
*Size.*—Averaging 3 mm in width and 20 mm in length.
*Splitting.*—The calyx does not split.
*Aspect.*—Smooth.
*Color.*—RHS 137-D.

THE FLOWER

Blooming habit: Intermittent and profuse, from Spring through Fall.
Size of flower: Small.
*Diameter.*—Averaging about 35 mm.
*Depth.*—Averaging about 5 mm.
Borne: In a cluster.
Shape:
*When first opening.*—Flat.
*When mature.*—Flat.
Number of flowers per main flower stem: 25–30.
Petalage:
*Number of petals.*—5.
*Arrangement.*—Side by side around the pistil.

*Form.*—Fan-shaped.
*Texture.*—Soft.
*Appearance.*—Velvety.
*Margins.*—Dentate.
*Apex.*—Deep incisions.
*Color.*—The color of the petals (when the sepals first divide) is RHS 57-A/B. The color of the petals when they first begin to unfurl is RHS 57-A/B. The inner "mottled" portion of the petal is RHS 57-A and the outer portion is RHS 57-B. The "mottled" portion also contains 30–50 small spots colored RHS 155-D. The color of the base is RHS 155-D. The color of the reverse side is RHS 62-A.
Flower stem:
*Length.*—80–110 cm.
*Character.*—Strong and upright.
*Color.*—RHS 137-C.
*Fragrance.*—Yes.
Discoloration after full bloom: Slight.
Persistence: The flowers hang on and dry.
Disease resistance: Resistant to *Fusarium oxysporum,* as observed at Aalsmeer.
Lasting quality: Averaging about 12 days as a cut flower and 21 days on the plant.
Changes with maturity: Young flowers are colored RHS 57-B for the outer portion of the petals and RHS 57-A for the inner "mottled" portion of the petal. The "mottled" portion also contains 30–50 small spots which are colored RHS 155-D. When the flowers age, the outer portion of the petal turns to RHS 57C and the "mottled" portion turns to RHS 57-C. The small spots in the "mottled" portion remain RHS 155-D.

REPRODUCTIVE ORGANS

Stamens: None.
Anthers: None.
Filaments: None.
Pistils:
*Number.*—1.
Styles:
*Length.*—About 22 mm. in average.
*Color.*—RHS 64-B.
Stigmas:
*Color.*—RHS 64-B.

FRUIT

Fertility: The fruit is not fertile.
Shape: Pear-shaped.

I claim:

1. The new and distinctive miniature spray carnation plant, substantially as herein shown and described, particularly characterized by its small flat tyrian-purple flowers, which are produced profusely in clusters on strong, erect branches of the main stem of a tall, upright bush.

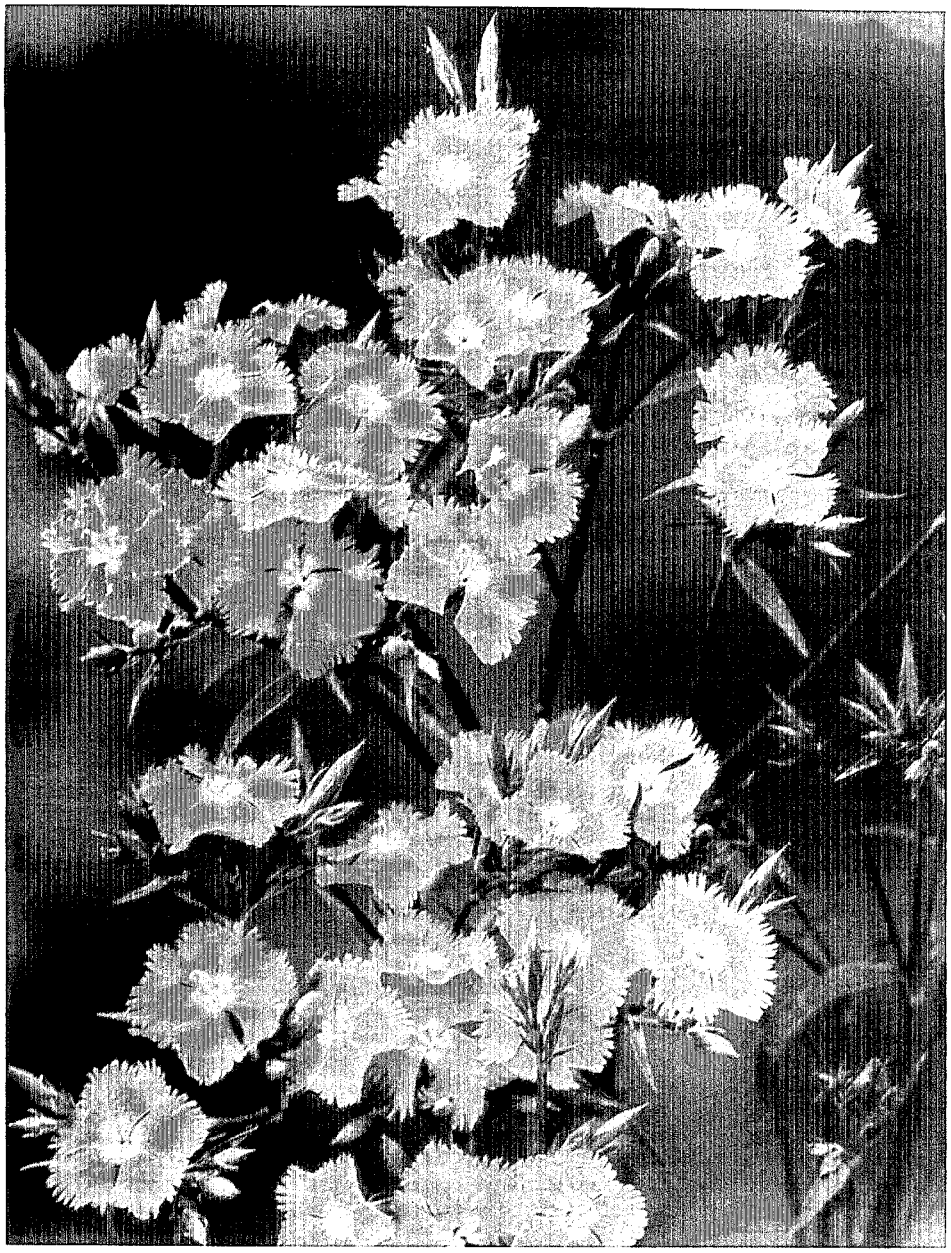

* * * * *